United States Patent [19]

Yamamoto

[11] Patent Number: 4,990,532

[45] Date of Patent: Feb. 5, 1991

[54] EXTERNAL PREPARATIONS

[75] Inventor: Shinji Yamamoto, Fukuoka, Japan

[73] Assignee: Sansho Seiyaku Co., Ltd., Fukuoka, Japan

[21] Appl. No.: 184,527

[22] Filed: Apr. 22, 1988

[30] Foreign Application Priority Data

Apr. 30, 1987 [JP] Japan ................................ 62-108226

[51] Int. Cl.$^5$ ................................................ A61K 31/35
[52] U.S. Cl. ..................................... 514/460; 514/844
[58] Field of Search ................................ 514/460, 844

[56] References Cited

PUBLICATIONS

Chem. Abst. 89:4582b, 1978.

Primary Examiner—John W. Rollins
Attorney, Agent, or Firm—Jordan and Hamburg

[57] ABSTRACT

External preparations containing, as active ingredient, kojic acid purified by sublimation show higher stability against discoloration with the passage of time compared with conventional products containing otherwise purified kojic acid.

8 Claims, 1 Drawing Sheet

EXTERNAL PREPARATIONS

BACKGROUND OF THE INVENTION

1. Field of the Invention

This invention relates to external preparations with improved stability against discoloration comprising kojic acid purified by sublimation.

2. Description of the Prior Art

Kojic acid is known as a substance capable of effectivity inhibiting the formation of melanin in the human skin.

Cosmetics have also been disclosed which utilize the melanogenesis inhibitory action of this acid (for example, Japanese Patent Kokai No. 53-3538, and Japanese Patent Publication No. 56-18569, No. 61 109705, No. 62-3820).

Also known are external preparations utilizing the melanogenesis-inhibitory, anti-inflammatory and analgesic actions of kojic acid (for example, Japanese Patent Publication No. 61-10447, No. 58-3446, No. 60-27648, and Japanese Patent Kokai No. 61-143313, No. 61-143314).

Kojic acid contained in these cosmetics and external preparations has been accepted as an excellent ingredient capable of inhibiting the formation of melanin with no side effect to the skin.

However, the external preparations containing kojic acid tend to become discolored with the passage of time, thus lowering their commodity value, unless careful considerations are given to the removal of metal ions from the water, materials and equipment used for the manufacture thereof, the pH of final products and other factors.

SUMMARY OF THE INVENTION

Intensive studies to prevent discoloration of external preparations containing kojic acid as active ingredient have led us to discover the unexpected fact that this problem can be solved if kojic acid purified by sublimation is used. This invention was accomplished on the basis of these findings.

DETAILED DESCRIPTION OF THE PREFERRED EMBODIMENTS

Figure 1:
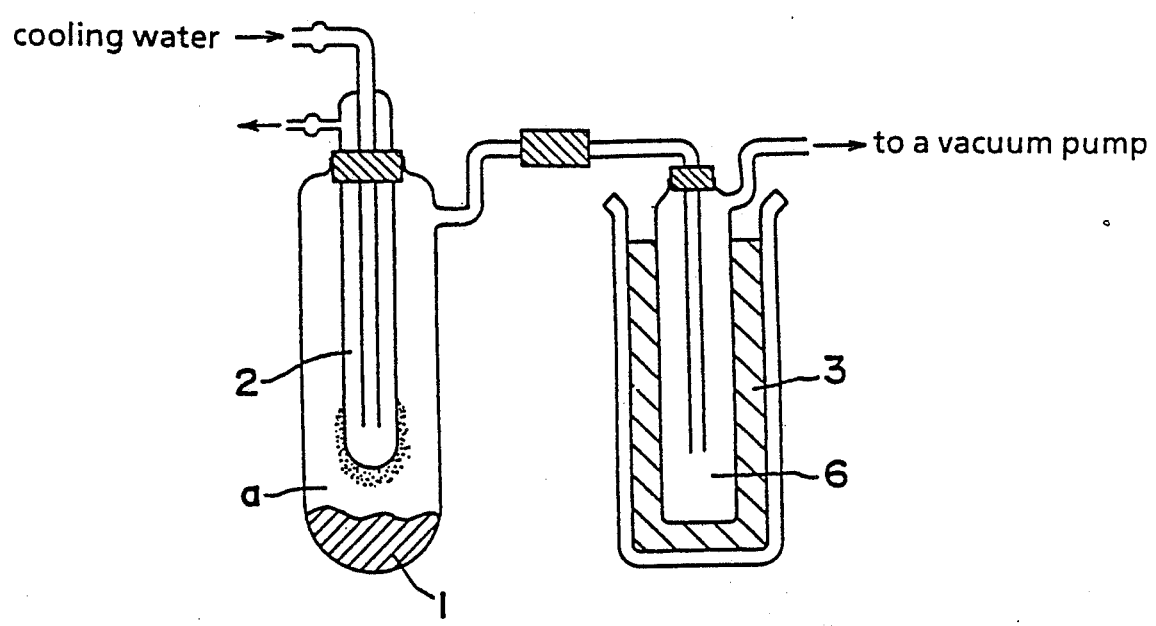
FIG. 1 illustrates the sublimation apparatus used in a Manufacturing Example for preparing purified kojic acid, in which a is a vessel for crude kojic acid, b is a trap, 1 is crude kojic acid being purified, 2 is an internal tube for cooling water circulation, and 3 is a freezing mixture.

This invention relates to external preparations containing, as active ingredient, kojic acid purified by sublimation which are free from discoloration with the passage of time.

Kojic acid used in this invention is obtained by growing a strain belonging to the genus Aspergillus, penicillium, Escherichia or Acetobacter and capable of producing kojic acid, and purifying the crude kojic acid recovered from the culture fluid by sublimation under normal or reduced pressure.

Sublimation may be carried out under normal pressure at a temperature ranging from 120° C. to the melting point of the acid. However, better results can be obtained by sublimation under reduced pressure at an elevated temperature in terms of product yield.

The external preparations herein mean general pharmaceutical preparations for external use, such as ointments, emulsions, lotions, creams, emulsified lotions, skin lotions and packs. Kojic acid purified by sublimation is contained in these preparations in amounts of 0.01 to 5.00 weight %.

Known techniques may be used for the manufacture of these preparations from the purified kojic acid and base materials for external preparations.

Kojic acid purified by sublimation shows the same effect of inhibiting melanogenesis as the acid conventionally used. It also exhibits similar synergistic effects with vitamin E, derivatives thereof, placental extract and liver extract.

Thus, the external preparations of this invention containing, as active ingredient, kojic acid purified by sublimation show higher stability against discoloration compared with conventional products containing otherwise purified kojic acid.

This invention will become more apparent from the following Examples and Manufacturing Example (purification of kojic acid by sublimation).

MANUFACTURING EXAMPLE

Kojic acid was purified by sublimation using an apparatus shown in FIG. 1. Powder of crude acid (2g) was placed at the bottom of vessel a fitted with an internal tube for cooling water circulation 2. Trap b was externally cooled with a freezing mixture 3 (acetone/dry ice), and the vessel a was evacuated to 5 torr by a vacuum pump and heated to 140° C. with its bottom immersed in an oil of appropriate depth. Treatment under the conditions described above gave sublimate of kojic acid deposited on the bottom of internal tube 2. This sublimate was collected eight times at 60-minute intervals. The total yield of purified acid was one gram.

The pure acid thus prepared has the following properties:

| | |
|---|---|
| (1) Appearance | white powder |
| (2) Melting point | 154.4° C. |
| (3) Color tone (3%), 420 nm | 0.002 (absorbance) |
| (4) Turbidity (3%), 570 nm | 0.002 (absorbance) |
| (5) pH (1%) | 4.57 |
| (6) Purity | 100.0% |

EXAMPLE 1

Skin Lotion

| | |
|---|---|
| Polyethylene adduct of hardened castor oil (60 E.O.) | 1.00% |
| Ethanol | 15.00 |
| Methyl p-oxybenzoate | 0.10 |
| Citric acid | 0.10 |
| Sodium citrate | 0.30 |
| 1,3-Butylene glycol | 4.00 |
| Disodium edetate | 0.01 |
| Sublimed kojic acid | 0.50 |
| Pure water | Balance |

EXAMPLE 2

Emulsified Lotion

| | |
|---|---|
| Polyoxyethylene-sorbitan | 1.00% |

| -continued | |
| --- | --- |
| monostearate (20 E.O.) | |
| Polyoxyethylene-sorbitan tetraoleate (60 E.O.) | 0.50 |
| Lipophilic glycerol monostearate | 1.00 |
| Stearic acid | 0.50% |
| Behenyl alcohol | 0.50 |
| Avocado oil | 4.00 |
| Glycerol trioctanoate | 4.00 |
| Ethyl p-oxybenzoate | 0.20 |
| 1,3-Butylene glycol | 5.00 |
| Xanthan gum | 0.14 |
| Disodium edetate | 0.01 |
| Sublimed kojic acid | 1.00 |
| Pure water | Balance |

EXAMPLE 3

Cream

| | |
| --- | --- |
| Polyethylene glycol monostearate (40 E.O.) | 2.00% |
| Self-emulsifiable glycerol monostearate | 5.00 |
| Stearic acid | 5.00 |
| Behenyl alcohol | 1.00 |
| Liquid paraffin | 10.00 |
| Glycerol trioctanoate | 10.00 |
| p-Oxybenzoic acid ester | 0.20 |
| 1,3-Butylene glycol | 5.00 |
| Disodium edetate | 0.01 |
| Sublimed kojic acid | 1.00 |
| Pure water | Balance |

EXAMPLE 4

Cream Pack

| | |
| --- | --- |
| Polyethylene glycol monostearate (40 E.O.) | 2.00% |
| Self-emulsifiable glycerol monostearate | 5.00 |
| Stearic acid | 5.00 |
| Behenyl alcohol | 0.50 |
| Squalane | 15.00 |
| Cetyl octanoate | 5.00 |
| p-Oxybenzoic acid ester | 0.20 |
| 1,3-Butylene glycol | 5.00 |
| Disodium edetate | 0.01 |
| Sublimed kojic acid | 1.00 |
| Pure water | Balance |

Described below are tests on the stability of sublimed kojic acid and external preparations containing the same against discoloration.

(1) Test samples (a) Sublimed kojic acid obtained in the Manufacturing Example;

(b) Cream prepared in Example 3 containing 1% of the sublimed kojic acid;

(c) Kojic acid purified by a method other than sublimation; and (d) Cream prepared according to the formulation of Example 3 in which the sublimed kojic acid is replaced with kojic acid purified by a method other than sublimation

(2) Testing procedure

Each of the samples (10g) was filled in a glass bottle and allowed to stand at 45° C. for 30 days. Color of each sample was visually observed at the start of test, and on the 5th, 10th, 20th and 30th days.

(3) Result

The results of the test are summarized in the table below.

| Sample | At start | 5th day | 10th day | 20th day | 30th day |
| --- | --- | --- | --- | --- | --- |
| a | — | — | — | ± | + |
| b | — | — | — | ± | ± |
| c | — | ± | + | ++ | ++ |
| d | — | ± | + | ++ | +++ |

—No discoloration; ±: Faint yellowing;
+Slight yellowing; ++: Appreciable yellowing As is apparent from the table, the external preparations containing kogic acid purified by sublimation showed higher stability against discoloration.

What is claimed is:

1. A composition for external application to skin containing, as an active ingredient, a sublimate of kojic acid, said sublimiate comprising a pure white powder having a melting point of 154.4° C., a purity of 100%, a color tone (3%) absorbance of 0.002 at 420 nm, a turbidity (3%) absorbance of 0.002 at 570 nm and a pH of 4.57, and an incipient as a carrier for said active ingredient.

2. A composition for external application to skin containing, as an active ingredient, a sublimate of kojic acid produced by the process of sublimating crude kojic acid by heating under normal or reduced pressure, and an incipient as a carrier for said active ingredient.

3. A process for preventing discoloration of a composition for external application to skin, said composition containing kojic acid as an active ingredient, comprising sublimating crude kojic acid by heating under normal pressure at a temperature ranging from 120° C. to the melting point of said kojic acid to produce a sublimiate of kojic acid, and preparing a composition for external application to skin including therein 0.01 to 5.0 weight % of said sublimate of kojic acid as an active ingredient and an incipient as a carrier for said active ingredient.

4. A process as in claim 3, wherein said composition is selected from the group consisting of an ointment, an emulsion, a lotion, a cream, an emulsified lotion, a skin lotion and a pack.

5. The product produced by the process according to claim 3.

6. A process for preventing discoloration of a composition for external application to skin, said composition containing kojic acid as an active ingredient, comprising sublimiating crude kojic acid by heating under reduced pressure at an elevated temperature to produce a sublimate of kojic acid, and preparing a composition for external application to skin including therein 0.01 to 5.0 weight % of said sublimate of kojic acid as an active ingredient and an incipient as a carrier for said active ingredient.

7. A process as in claim 6, wherein said composition is selected from the group consisting of an ointment, an emulsion, a lotion, a cream, an emulsified lotion, a skin lotion and a pack.

8. The product produced by the process according to claim 6.

* * * * *